United States Patent
Gadakar et al.

(10) Patent No.: US 10,710,999 B2
(45) Date of Patent: Jul. 14, 2020

(54) POLYMORPH OF AN INTERMEDIATE FOR PALBOCICLIB SYNTHESIS

(71) Applicant: MYLAN LABORATORIES LIMITED, Hyderabad (IN)

(72) Inventors: Mahdeshkumar Gadakar, Hyderabad (IN); Dnyandeo Punde, Hyderabad (IN); Rajendra Yadav, Hyderabad (IN); Yogesh Wakchaure, Hyderabad (IN)

(73) Assignee: MYLAN LABORATORIES LIMITED (IN)

( * ) Notice: Subject to any disclaimer, the term of this patent is extended or adjusted under 35 U.S.C. 154(b) by 0 days.

(21) Appl. No.: 16/338,832

(22) PCT Filed: Oct. 4, 2017

(86) PCT No.: PCT/IN2017/050446
§ 371 (c)(1),
(2) Date: Apr. 2, 2019

(87) PCT Pub. No.: WO2018/065999
PCT Pub. Date: Apr. 12, 2018

(65) Prior Publication Data
US 2019/0225608 A1 Jul. 25, 2019

(30) Foreign Application Priority Data
Oct. 7, 2016 (IN) .............................. 201641034492

(51) Int. Cl.
*C07D 471/04* (2006.01)
(52) U.S. Cl.
CPC ........ *C07D 471/04* (2013.01); *C07B 2200/13* (2013.01)

(58) Field of Classification Search
CPC .................................................... C07D 471/04
See application file for complete search history.

(56) References Cited

FOREIGN PATENT DOCUMENTS

| | | |
|---|---|---|
| CN | 105924439 A | 9/2016 |
| WO | 2014128588 A | 8/2014 |

OTHER PUBLICATIONS

Anon. (IP.com Journal (2015), 15(11B), 1-2 (No. IPCOM000244148D), Nov. 15, 2015).*
Mark T. Maloney et al: "Palbociclib Commercial Manufacturing Process Development. Part II: Regioselective Heck Coupling with Polymorph Control for Processability"; Organic Process Research and Development vol. 20, No. 7, Jul. 15, 2016.
PCT International Search Report for application PCT/IN2017/050446, dated Apr. 12, 2018.
PCT Written Opinion of the International Searching Authority for application PCT/IN2017/050446, dated Apr. 12, 2018.
Hilfiker R (Editor) Ed, "Polymorphism in the Pharmaceutical Industry", Jan. 1, 2006, pp. 1-19, XP002528052, ISBN: 978-3-527-31146-0.
Caira Ed, Montchamp Jean-Luc, "Crystalline Polymorphism of Organic Compounds", Topics in Current Chemistry, Springer, Berlin DE, vol. 198, Jan. 1, 1998, pp. 163-208, XP008166276, ISSN: 0340-1022.

* cited by examiner

*Primary Examiner* — Bruck Kifle

(57) ABSTRACT

The present disclosure provides a novel polymorph of an intermediate useful in the preparation of palbociclib. The polymorph has enhanced properties that influence process ability of the intermediate and synthesis of palbociclib.

7 Claims, 1 Drawing Sheet

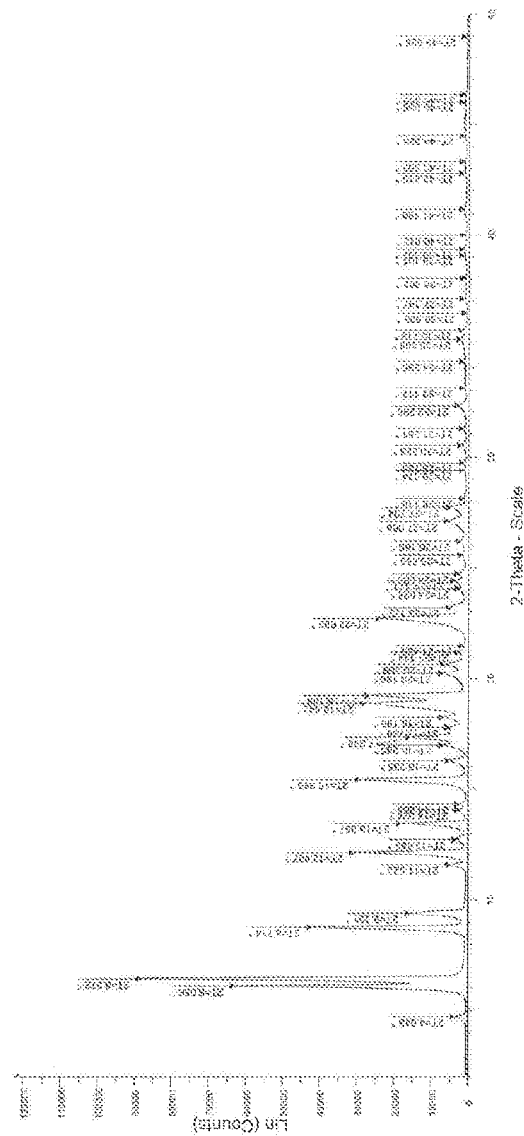

POLYMORPH OF AN INTERMEDIATE FOR PALBOCICLIB SYNTHESIS

CROSS-REFERENCE TO RELATED APPLICATIONS

This application is a national stage entry under 35 U.S.C. § 371 of International Application PCT/IN2017/050446, with an international filing date of Oct. 4, 2017, which claims the benefit of earlier Indian provisional patent application no. 201641034492 filed on October 7, 2016, which is incorporated and incorporates the PCT and Indian applications into the current application by reference in their entirety.

BACKGROUND OF THE INVENTION

Field of the Invention

The present invention relates generally to active pharmaceutical ingredients and more specifically to a novel polymorph of Form M of an intermediate that may be used to prepare palbociclib, namely, Formula-2 as named and disclosed herein. The present invention also provides methods for the preparation of the intermediate.

Background of the Invention

Palbociclib (PD-0332991) is a potent and selective inhibitor of CDK4 and CDK6. Palbociclib is chemically known as 6-acetyl-8-cyclopentyl-5-methyl-2-{[5-(piperazin-1-yl)pyridin-2yl]amino}pyrido[2,3-d]pyrimidin-7(8H)-one and represented by Formula-1.

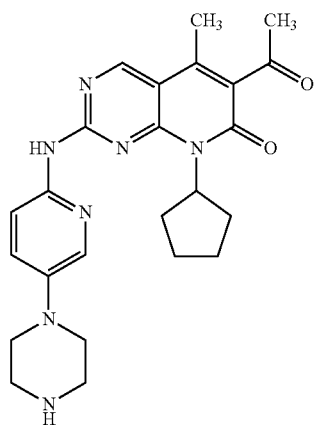

Formula-1

Palbociclib is marketed in the United States under the tradename IBRANCE, indicated for the treatment of HR+, HER2− advanced ormetastatic breast cancer in combination with an aromatase inhibitor as initial endocrine based therapy in postmenopausal women, or fulvestrant in women with disease progression following endocrine therapy.

Palbociclib and pharmaceutically acceptable salts thereof are disclosed in International Publication No. WO 2003/062236 and U.S. Pat. Nos. 6,936,612; 7,208,489; and 7,456,168, which discloses the preparation of palbociclib hydrochloride.

International Publication No. WO 2005/005426 and U.S. Pat. Nos. 7,345,171 and 7,863,278 disclose the preparation of the free base and various mono- and di-acid addition salts of palbociclib, including polymorphic forms of the isethionate salt of palbociclib.

International Publication No. WO2014128588A1 discloses several polymorphic forms Form-A, Form-B, and Form-C of a compound illustrated below as Formula-2. Formula-2 may be utilized in the preparation of palbociclib.

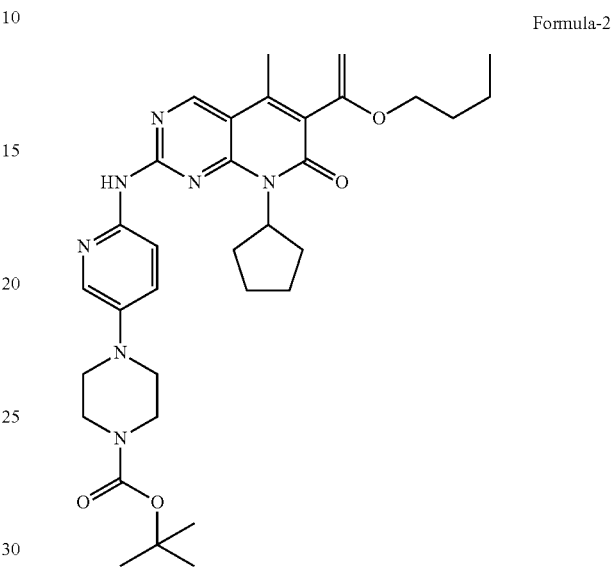

Formula-2

The present invention provides a novel polymorph Formula-2 that has improved filterability, improved drying, and improved purity when scaled up for industrial or commercial preparation.

SUMMARY OF THE INVENTION

In one aspect, the present invention provides crystalline Form M of Formula-2, shown below.

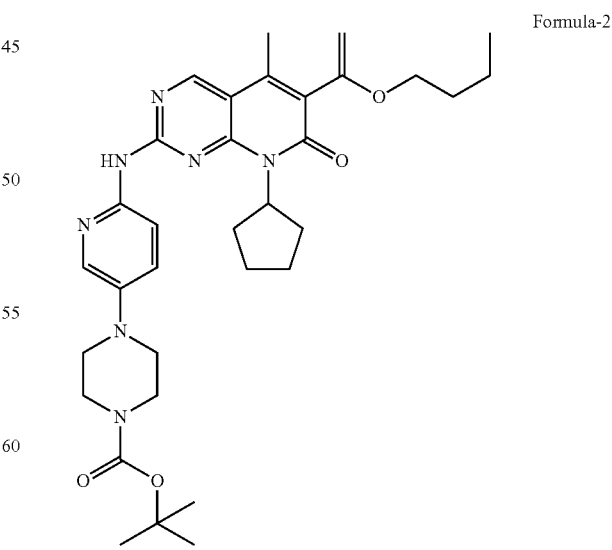

Formula-2

Within the context of the invention, Form M of Formula-2, prepared by methods disclosed herein, may be characterized by a powder X-ray diffraction pattern having peaks at 6.0 and 8.7±0.2°2θ. Crystalline FormM of Formula-2 may be further characterized by a powder X-ray diffraction pattern having peaks at 6.0, 6.3, 8.7, 12.0, 15.3, 19.1, and 22.6±0.2°2θ. Crystalline FormM of Formula-2 may be further characterized by the powder X-ray diffraction pattern of in FIG. 1.

In another aspect, the present invention provides a process for preparing crystalline Form M of Formula-2.

In one embodiment, crystalline Form M of Formula-2 may be prepared by a process that includes the steps of:
a) dissolving a compound of Formula-2 in a solvent to form a reaction mixture;
b) heating the reaction mixture;
c) optionally adding a seed of Form M of Formula-2;
d) slowly cooling the reaction mixture; and
e) isolating crystalline Form M of Formula-2.

Within the context of this embodiment, the solvent may be, for example, an alcohol, tetrahydrofuran, or mixtures thereof. Examples of suitable alcohols include, but are not limited to, methanol, ethanol, isopropanol, and mixtures thereof.

Within the context of the present embodiment, the reaction mixture is heated to a temperature of 65° C. to 110° C. in the heating step and cooled to 15° C. to 20° C. in the cooling step.

In another aspect, the present invention provides crystalline Form M of Formula-2 having a purity of 99.0%.

Within the context of the present invention, crystalline Form M of Formula-2 may be converted to palbociclib.

BRIEF DESCRIPTION OF THE FIGURES

Further aspects of the present disclosure together with additional features contributing thereto and advantages accruing there from will be apparent from the following description of embodiments of the disclosure which are shown in the accompanying drawing wherein:

FIG. 1 shows a powder X-ray diffraction (PXRD) pattern of Form M of Formula-2.

DETAILED DESCRIPTION OF THE INVENTION

In one aspect, the present invention provides Form M of Formula-2, shown below.

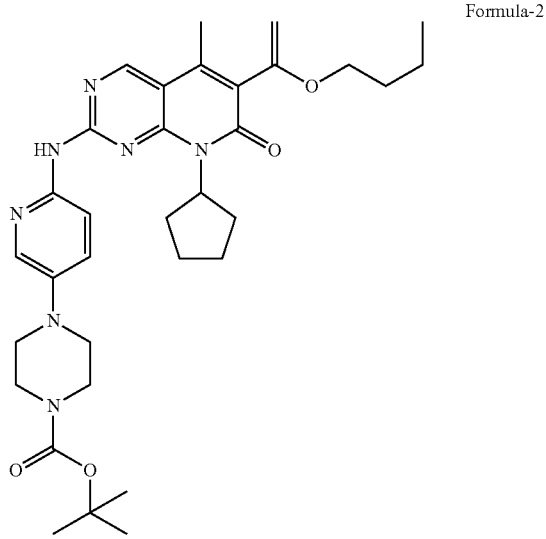 [SMILES: C=C(OCCCC)c1c(C)c2cnc(Nc3ccc(N4CCN(C(=O)OC(C)(C)C)CC4)cn3)nc2n(C2CCCC2)c1=O]

Formula-2

Crystalline Form M of Formula-2 disclosed herein may be characterized by X-ray powder diffraction (PXRD). Thus, samples of crystalline Form M of Formula-2, prepared by methods disclosed herein, were analyzed on a Bruker D8 discover powder X-ray diffractometer equipped with goniometer of θ/2θ configuration and LynxEye detector. The Cu-anode X-ray tube was operated at 40 kV and 30 mA. The experiments were conducted over the 2θ range of 2.0°-50.0°, 0.030° step size, and 0.4 seconds' step time.

In one embodiment, crystalline Form M of Formula-2 may be characterized by a PXRD pattern having significant peaks at 6.0, 6.3, 8.7, 12.0, 15.3, 19.1, and 22.6±0.2°2θ.

Crystalline FormM of Formula-2 maybe further characterized by the PXRD pattern depicted in FIG. 1.

In another aspect, the present invention provides a process for the preparation of crystalline Form M of Formula-2.

In one embodiment, crystalline Form M of Formula-2 may be prepared by a process that includes the steps of:
a) dissolving Formula-2 in a solvent to form a reaction mixture;
b) heating the reaction mixture;
c) optionally adding a seed of crystalline Form M of Formula-2;
d) slowly cooling the reaction mixture, and
e) isolating crystalline Form M of Formula-2.

According to the present embodiment, Formula-2 may be dissolved in a solvent. Examples of suitable solvents include, but are not limited to, alcohols, ethers, and mixtures thereof. Examples of suitable alcohols include, but are not limited to, methanol, ethanol, isopropanol, and mixtures thereof. One suitable ether solvent is tetrahydrofuran, though others may be useful. One of skill in the art would be able to predict what alcohol and ether solvents would be useful within the context of this embodiment.

Next, the reaction mixture may be heated. Within the context of this embodiment, the solution may be heated to about 60° C. to about 110° C.

Optionally, seeds of crystalline Form M of Formula-2 may be added.

Next, the reaction mixture may be gradually cooled. Within the context of this embodiment, the reaction mixture is cooled slowly, for example by reducing the temperature to about 15° C. to about 20° C. at the rate of 10° C. per hour under stirring.

Within the context of the invention, the term "about" when modifying an absolute measurement, such as time, mass, or volume, is meant to mean the recited value plus or minus 10% of that value. Within the context of the invention, the term "about" when modifying a temperature measurement is meant to mean the recited temperature plus or minus five degrees.

Crystalline Form M of Formula-2 may then be isolated. This may be carried out by methods well known in the art, for example, by filtering the reaction mixture to obtain a solid. The solid may be further processed, for example, by drying, to obtain the final crystalline Form M of Formula-2.

Within the context of the present invention, crystalline Form M of Formula-2 may be further converted to palbociclib or pharmaceutically acceptable salts thereof.

Crystalline Form M of Formula-2 prepared according to methods disclosed herein may display properties that are improved over prior art polymorphs of Formula-2. For example, Form M of Formula-2 is easy to filter. Use of Form M of Formula-2 as an intermediate in the preparation of palbociclib enhances the yield and purity of the final palbociclib material.

The following examples are illustrative of some of the embodiments of the invention described herein. These examples should not be considered to limit the spirit or scope of the invention in any way.

EXAMPLES

Example 1: Preparation of Formula-2

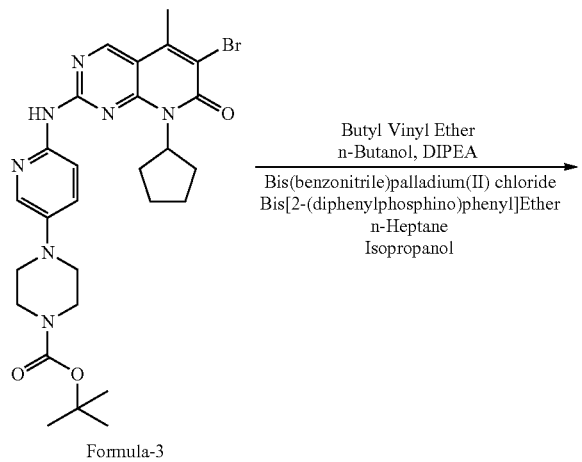

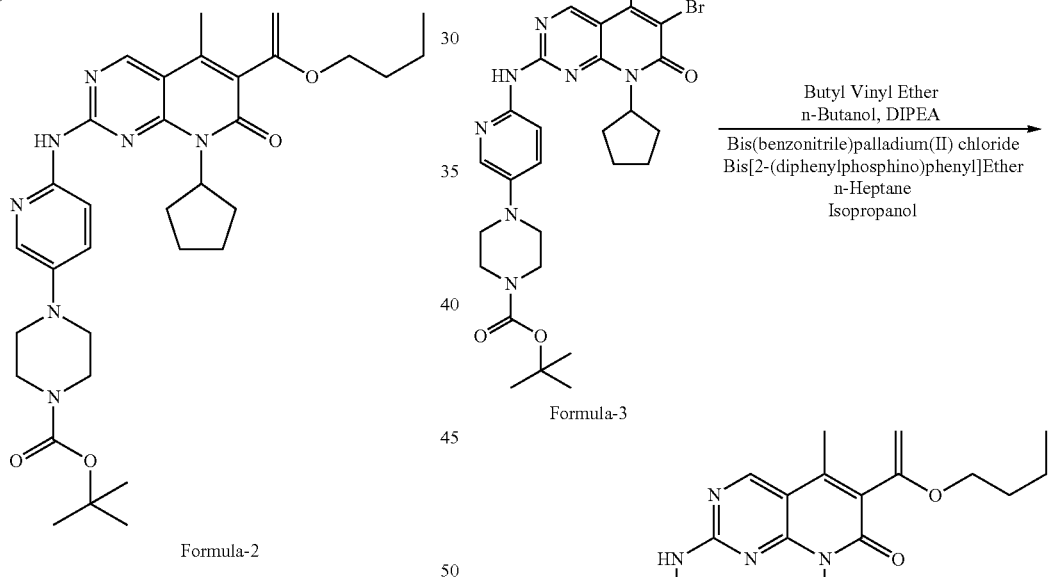

Butyl vinyl ether (185.94 ml, 6 eq. moles) was added to a stirred suspension of Formula-3 (140 g, 0.2395 moles, 1 eq.) and n-butanol (2800 ml, 20.0V) in a round bottom flask at 25-30° C. held under nitrogen atmosphere. Diisopropylethylamine (200.25 ml, 4.8 eq.) and bis(benzonitrile)palladium (II) chloride (9.18 g, 0.1 eq.) were charged into the reaction mass under stirring and the reaction mass was stirred for 10-15 minutes. Bis[2-(diphenylphosphino)phenyl] ether (38.69 g, 0.3 eq.) was added to the stirred slurry and further stirred for 10-15 minutes. The reaction mass was heated to 90-100° C. for 30 minutes after which the temperature was raised to 105-115° C. and stirred for 1 hour. After completion of the reaction, the mixture was cooled to 80-90° C. and water (210 ml, 1.5 V) was added slowly into the reaction mixture. Charcoal was charged into the reaction mixture. The hot solution was filtered through a 0.45-micron paper and washed with hot n-butanol (100 ml, 1.0 V). The filtrate was distilled out under vacuum to obtain a residue which was swapped with n-heptane (1400 ml×2). n-Heptane (1400 ml, 10.0 V) was added to the residue and the mixture was stirred for 60-70 minutes. The solution was filtered and the obtained solid was washed with n-heptane (200 ml, 2.0 V) and suck dried to obtain a wet cake.

The wet cake was charged into isopropanol (2500 ml, 25.0 V) and heated to 65-70° C. to get a clear solution. Charcoal (10 g, 10% w/w) was added to the clear solution which was then filtered through Celite and washed with hot isopropanol (200 ml, 2.0 V). The two filtrate volumes were combined and heated to 65-70° C. to get a clear solution. The reaction mixture was gradually cooled to 58-62° C., seeded with crystalline Form M of Formula-2 (2.0 g, 2% w/w) and stirred for 2 hours at 58-62° C. The reaction mixture was gradually cooled to 48-52° C. and stirred for 2 hours after which it was further cooled to 28-32° C. and stirred for another 2 hours. The reaction mixture was cooled to 15-20° C. and stirred for another 2 hours. The solution was filtered, and the solid product was washed with isopropanol (200 ml, 2.0 V). The resulting product was dried at 55-60° C. under vacuum for 6-8 hours to give Formula-2 (98.0 g, 68% yield) as a yellow solid. HPLC Purity: 99.00%

Example 2: Preparation of Formula-2

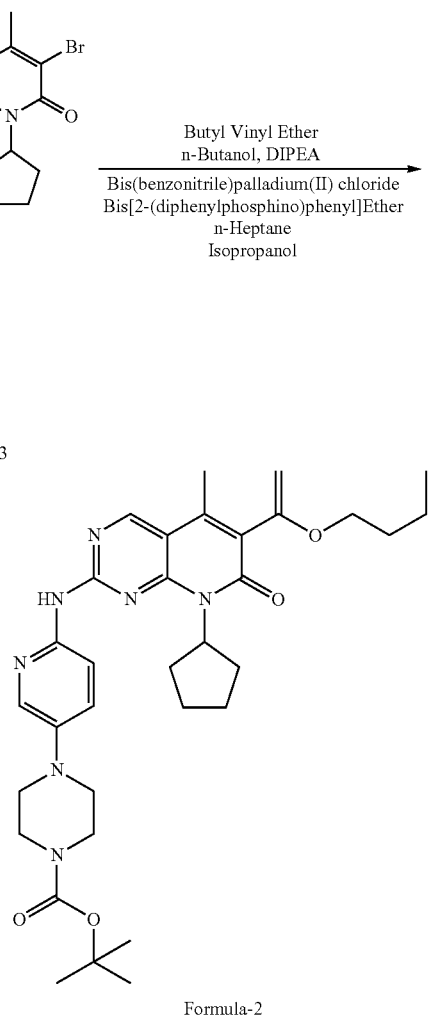

Butyl vinyl ether (185.94 ml, 6 eq. moles) was added to a stirred suspension of Formula-3 (140 g, 0.2395 moles, 1 eq.) and n-butanol (2800 ml, 20.0 V) in a dry round bottom flask at 25-30° C. under nitrogen atmosphere. Diisopropylethylamine (200.25 ml, 4.8 eq.) and bis(benzonitrile)palladium (11) chloride (9.18 g, 0.1 eq.) were charged into the reaction mass under stirring and the reaction mass was stirred for 10-15 minutes. Bis[2-(diphenylphosphino)phenyl]ether (38.69 g, 0.3 eq.) was added to the slurry and further stirred for 10-15 minutes. The reaction mass was heated to 90-100° C. for 30 minutes. The temperature was raised to 105-115° C. and stirred for 1 hour. After completion of the reaction, the mixture was cooled to 80-90° C. and added water (210 ml, 1.5 V) slowly into reaction mixture. Charcoal was charged into the reaction mixture. The hot solution was filtered through 0.45-micron paper and washed with hot n-butanol (100 ml, 1.0 V). The filtrate was distilled under vacuum to get a residue which was swiped with n-heptane (1400 ml×2). n-Heptane (1400 ml, 10.0 V) was added and the mixture was stirred for 60-70 minutes. The mixture was filtered and the product was washed with n-heptane (200 ml, 2.0 V) and suck dried to result in a wet cake.

The wet cake was charged into isopropanol (2500 ml, 25.0 V) and the mixture was heated to 65-70° C. to get a clear solution. Charcoal (10 g, 10% w/w) was added to the clear solution which was filtered through Celite, then washed with hot isopropanol (200 ml, 2.0 V). Filtrate combined, heated to 65-70° C. to get a clear solution. The reaction mixture was gradually cooled to 58-62° C. and stirred for 2 hours at the same temperature. The reaction mixture was gradually cooled to 48-52° C. and stirred for 2 hours. It was then further cooled to 28-32° C. and stirred for 2 hours before cooling yet again to 15-20° C. and stirring for another 2 hours. The mixture was filtered and the resultant product was washed with isopropanol (200 ml, 2.0 V). The resulting product was dried at 55-60° C. under vacuum for 6-8 hours to give Formula-2 (98.0 g, 68%) as a yellow solid. HPLC Purity: 99.00%

Example 3: Preparation of Palbociclib Dihydrochloride Dihydrate

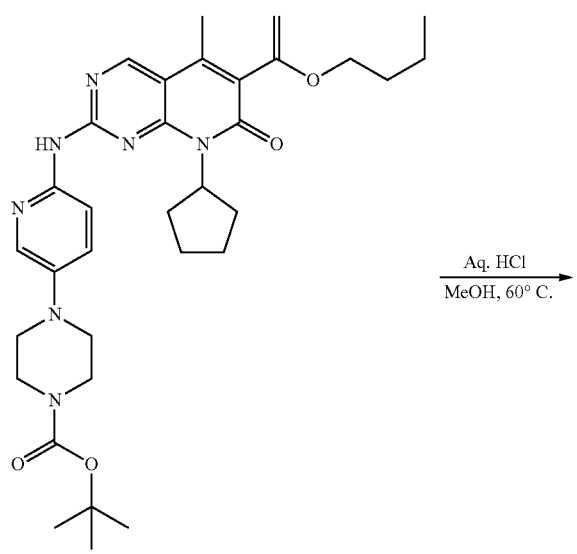

Formula-2

Aq. HCl
MeOH, 60° C.

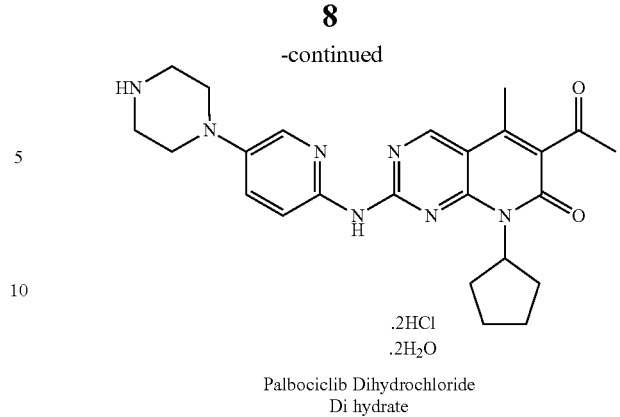

.2HCl
.2H$_2$O

Palbociclib Dihydrochloride
Di hydrate

Concentrated HCl (96 ml) was added dropwise to a mixture of Formula-2 (60 g), methanol (1500 ml), and water (24 ml) at 20-30° C. under stirring. The reaction mixture was heated to 40-45° C. and maintained for 1 hour. The temperature was increased to 60-65° C. and stirred for 4 hours. The reaction mixture was cooled to 50-55° C. and THF (1500 ml) was added slowly, maintaining the temperature. The reaction mixture was cooled to 20-30° C. The reaction mixture was stirred at 20-30° C. for 15 minutes then the temperature was reduced to 7-13° C. and stirred for 3 hours. The solution was filtered and the solid product was washed with diisopropylether (120 ml). The wet cake was suck dried at 20-30° C. for 1 hour then transferred into a clean, dry round bottom flask. Methanol (1200 ml) was charged, followed by aqueous solution of HCl (96 ml) slowly under stirring. Water (60 ml) was added to the reaction mixture then heated to 60-65° C. The mixture was stirred at 60-65° C. for 30 minutes then cooled to 55-60° C. THF (1200 ml) was added slowing while maintaining the temperature. The mixture was stirred at 55-60° C. for 15 minutes, cooled to 7-13° C., and stirred for 3 hours. The mixture was filtered and the product was washed with diisopropylether (300 ml). The solid was then suck dried at 20-30° C. for 30 minutes and dried under vacuum at 50-55° C. for 6 hours to get substantially pure palbociclib dihydrochloride dihydrate as a yellow solid (50 g, 90%, Purity by HPLC>99.8%)

Example 4: Preparation of Palbociclib

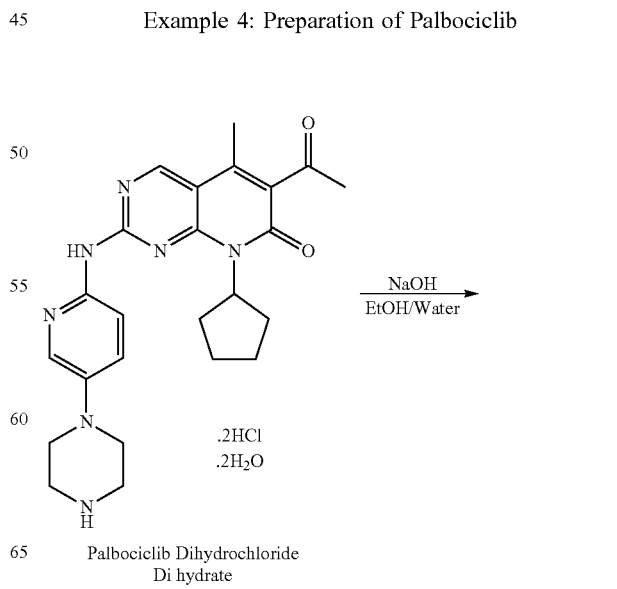

NaOH
EtOH/Water

.2HCl
.2H$_2$O

Palbociclib Dihydrochloride
Di hydrate

-continued

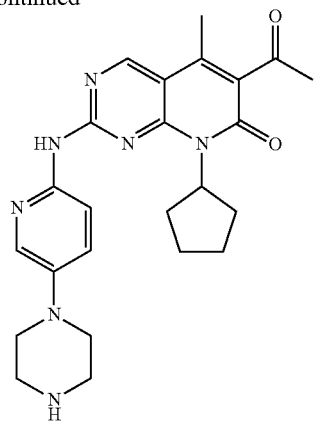

Palbociclib

Palbociclib dihydrochloride dihydrate (45 g) was dissolved in water (427.5 ml) and ethanol (127.5 ml) while stirring the solution at 20-25° C. Aqueous sodium hydroxide solution (7.4 g in 90 ml) was added dropwise at 19-25° C. The resulting mixture was stirred at 20-25° C. for 21 hours then filtered. The solid collected was washed with water (450 ml) followed by acetone (450 ml) and n-heptane (675 ml). The solid was then suck dried at 20-30° C. for 2 hours and dried under vacuum at 50-55° C. for 6 hours to get substantially pure palbociclib as a yellow solid (34 g, 94%, Purity by HPLC>99.8%)

We claim:

1. Crystalline Form M of a compound of Formula-2

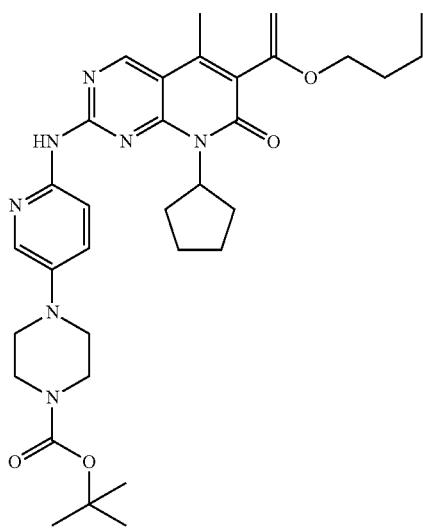

Formula-2 characterized by a powder X-ray diffraction pattern having peaks at 6.0 and 8.7±0.2°2θ.

2. The crystalline Form M of Formula-2 as in claim 1 further characterized by a powder X-ray diffraction pattern having peaks at 6.0, 6.3, 8.7, 12.0, 15.3, 19.1, and 22.6±0.2°2θ.

3. The crystalline Form M of Formula-2 as in claim 1, further characterized by the powder X-ray diffraction pattern of in FIG. 1.

4. A process for the preparation of crystalline Form M of Formula-2, as in claim 1, comprising the steps of:

a) dissolving a compound of Formula-2 in a solvent selected from the group consisting of alcohols, tetrahydrofuran, and mixtures thereof to form a reaction mixture;

b) heating the reaction mixture;

c) optionally adding a seed of Form M of Formula-2;

d) slowly cooling the reaction mixture; and 3) isolating crystalline Form M of Formula-2.

5. The process of claim 4, wherein the alcohol is selected from the group consisting of methanol, ethanol, isopropanol, and mixtures thereof.

6. The process of claim 4, wherein the reaction mixture is heated to 110° C. in the heating step and wherein the reaction mixture is cooled to 15° C. in the cooling step.

7. Crystalline Form M of Formula-2 prepared according to the process pf claim 4, further having a purity of 99.0%.

* * * * *